United States Patent
Nasser-Ghodsi et al.

(10) Patent No.: US 6,810,105 B2
(45) Date of Patent: Oct. 26, 2004

(54) METHODS AND APPARATUS FOR DISHING AND EROSION CHARACTERIZATION

(75) Inventors: Mehran Nasser-Ghodsi, Hamilton, MA (US); Phil Wood, Litchfield, NH (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 40 days.

(21) Appl. No.: 10/242,496

(22) Filed: Sep. 12, 2002

(65) Prior Publication Data

US 2003/0142782 A1 Jul. 31, 2003

Related U.S. Application Data

(60) Provisional application No. 60/351,960, filed on Jan. 25, 2002.

(51) Int. Cl.$^7$ .............................................. G01N 23/223
(52) U.S. Cl. ......................................... 378/44; 250/306
(58) Field of Search ............................... 250/310, 307, 250/492.3, 306; 378/44, 45, 46; 356/237.1, 237.2, 237.3, 237.4, 237.5

(56) References Cited

U.S. PATENT DOCUMENTS

| | | |
|---|---|---|
| 4,162,528 A | 7/1979 | Maldonado et al. |
| 4,472,825 A | 9/1984 | Jenkins |
| 4,476,386 A | 10/1984 | Reid et al. |
| 4,534,049 A | 8/1985 | Koga |
| 4,675,889 A | 6/1987 | Wood et al. |
| 4,777,364 A | 10/1988 | Sartore |
| 4,885,465 A | 12/1989 | Nagatsuka et al. |
| 4,959,848 A | 9/1990 | Parobek |
| 4,962,516 A | 10/1990 | Soezima |
| 5,055,679 A | 10/1991 | Ninomiya et al. |
| 5,060,247 A | 10/1991 | Watanabe |
| 5,065,020 A | 11/1991 | Kanda |
| 5,210,414 A | 5/1993 | Wallace et al. |
| 5,299,252 A | 3/1994 | Takahashi |
| 5,350,921 A | 9/1994 | Aoyama et al. |
| 5,485,499 A | 1/1996 | Pew et al. |
| 5,530,732 A | 6/1996 | Takemi |
| 5,594,246 A | 1/1997 | Sudo et al. |
| 5,596,195 A | 1/1997 | Obori et al. |
| 5,656,812 A | 8/1997 | Takahashi |
| 5,657,363 A | 8/1997 | Hossain et al. |
| 5,703,361 A | 12/1997 | Sartore |
| 5,705,878 A | 1/1998 | Lewis et al. ................. 310/328 |
| 5,754,620 A | 5/1998 | Hossain et al. |
| 5,777,336 A | 7/1998 | Silver et al. |
| 5,866,903 A | 2/1999 | Morita et al. |
| 5,877,498 A | 3/1999 | Sugimoto et al. |
| 5,892,809 A | 4/1999 | Wittry |
| 5,926,522 A | 7/1999 | McCarthy et al. |
| 6,108,398 A | 8/2000 | Mazor et al. |
| 6,351,516 B1 * | 2/2002 | Mazor et al. .................. 378/44 |
| 6,353,222 B1 * | 3/2002 | Dotan ......................... 250/310 |
| 6,421,122 B2 | 7/2002 | Nara et al. |

FOREIGN PATENT DOCUMENTS

JP       6-267485       9/1994

OTHER PUBLICATIONS

J.L. Pouchou and F. Pichoir, "Electron Probe X–Ray Microanalysis Applied To Thin Surface Films and Stratified Specimens", Scanning Microscopy, Supplement 7., (1993), pp. 167–189.

(List continued on next page.)

*Primary Examiner*—Edward J. Glick
*Assistant Examiner*—Hoon Song
(74) *Attorney, Agent, or Firm*—Beyer Weaver & Thomas, LLP

(57) ABSTRACT

The present invention includes a system for efficient and effective detection and characterization of dishing and/or erosion. An x-ray emission inducer is used to scan a target on a sample. The target can be scanned at an acute incident angle to allow characterization of the dishing and/or erosion and analysis of the metallization or thin film layer topology.

29 Claims, 8 Drawing Sheets

OTHER PUBLICATIONS

"High–Resolution X–ray Microanalysis for Low Voltage Applications", Noran Instruments, (1997), 5 pages.

M. Stavrev, D. Fischer, C. Wenzel, and T. Heiser, "Study OF Ta(N,O) diffusion barrier stability: analytical and electrical characterization of low level Cu contamination in Si", Microelectronic Engineering, 37/38 (1997) pp. 245–251.

JeanLouis Pouchou, "X–Ray microanalysis of stratified specimens", Elsevier Science Publishers B.V., Analytica Chimica Acta. 283 (1993) pp. 81–97.

Schiebl et al., "A characteristic fluorescence correction factor for use in electron probe microanalysis", Microsc. Microanal, Microstruct. 2, 1991, pp. 413–423.

S. Sevov et al., "A comparison of recently developed correction procedures for electron probe microanalysis", Scanning, 1989, vol. 11, pp. 123–134.

August et al., "A method for determining the mass thickness of thin films using electron probe microanalysis", Scanning, 1987, vol. 9, pp. 145–155.

August et al., "Energy distribution of electrons transmitted through thin foils", Institut fur Angewandte aund Technische Physik, Technische Universitat Wien Wiedner Hauptstr, 8–10, A–1040 Wien (Vienna), Austria.

Pfeiffer et al., "Models and their implementation", CEC–Vienna Reports, No. 92–08, Dec., 1992.

"MuFilm Data Collection & K–Ratio Measurement Documentation", pp. 2–10.

August et al., "Calculation and Comparison of the Surface Ionization", Institut fur Angewandte und Technische Physik, Technische Universitat Wien, Wiedner Hauptstr. 8–10, A–1040 Wien (Vienna), Austria.

August et al., "Calculation and Comparison of the Backscattering Factor R for Characteristic X–Ray Emission", Scanning, 1988, vol. 10, pp. 107–113.

August et al., "The Backscattering Factor as a Part of the Correction Procedures Employed in Quantitative Electron Probe Microanalysis", Radex–Rundschau, 1988, pp. 624–637.

August et al., "Calculation of the electron backscattering coefficient for thin films using a simple electron scattering model", J. Microsc. Spectrosc. Electron., 1989, vol. 14, pp. 189–201.

August, et al., "Theoretical prediction of the electron backscattering coefficient for multilayer structures", Journal of Microscopy, Feb. 1990, vol. 157, pp. 247–254.

* cited by examiner

METHODS AND APPARATUS FOR DISHING AND EROSION CHARACTERIZATION

CROSS-REFERENCE TO RELATED APPLICATIONS

This application claims priority under U.S.C. 119(e) of U.S. Provisional Application No.: 60/351,960 filed Jan. 25, 2002 entitled "METHODS AND APPARATUS FOR DISHING AND EROSION CHARACTERIZATION" by Mehran Nasser-Ghodsi and Phil Wood, the entirety of which is incorporated by reference in its entirety for all purposes.

The present application is related to U.S. patent application Ser. No. 09/990,171 by Mehran Nasser-Ghodsi and Anne Testoni, and titled Methods and Apparatus for Void Characterization and to U.S. patent application Ser. No. 09/990,170 by Mehran Nasser-Ghodsi and Jeffrey Reichert, and titled Methods and Apparatus for Defect Localization. Both of the above patent applications were filed on Nov. 21, 2001. The present application is also related to U.S. patent application Ser. No. 09/695,726 by Shing Lee, and titled Film Thickness Measurement Using E-Beam Induced X-Ray Microanalysis as of filing on Oct. 23, 2000. Each of the above noted applications are incorporated herein by reference for all purposes.

BACKGROUND OF THE INVENTION

1. Field of the Invention

The present invention generally relates to the field of inspection and analysis of specimens and, more particularly, to dishing and erosion inspection and analysis for semiconductor integrated circuits.

2. Description of Related Art

The metallization and thin film layers of conventional integrated circuits contain interconnects. The interconnects are arranged to allow electrical contact between transistors and other circuitry in an integrate circuit. However, dishing and erosion may cause defective interconnects on an integrated circuit. Dishing is the concavity formed near the center of an interconnect. Erosion is the deterioration of interconnects along with the surrounding material, typically an oxide. Processes such as chemical mechanical polishing (CMP) can cause dishing and erosion. Variation in polished surfaces (cuts, dishing and erosion) affect signal uniformity due to variation in the conductance of the Cu layer/lines.

During CMP, a dielectric layer comprising an oxide typically works to control CMP to material above the dielectric layer. However, the CMP process may nevertheless remove material in the dielectric layer. Conductive material removed from near the center of an interconnect is referred to as dishing. Conductive material as well as surrounding dielectric material removed from an interconnect is referred to as erosion.

Both erosion and dishing can negatively impact operation of integrated circuit devices by causing open circuits.

Inspection of integrated circuit at various stages of manufacture can significantly improve production yield and product reliability. If erosion or dishing can be detected early in production, various production processes such as CMP can be modified. For example, the slurry composition, plate and carrier rotational speeds, pad hardness, and the pressure of the polish head can be varied to improve processing.

Conventional surface abrasion systems use a protocol comprising of a fine needle traversing a surface, thereby indicating surface/topographical variations.

A secondary electron detector can also be used to measure the intensity of the secondary electron emission that originates only at the path swept by the scanning electron beam. A defective portion can be identified from the potential state of the portion under inspection. In one form of inspection, the mismatched portion between the defective voltage contrast image and the defect free one reveals the general defect location.

Other techniques involve slicing a wafer into cross sections and using an electron microscope to detect defects. Intrusive methods, however, are both time consuming and wasteful. Accoustic and optical methods are also available, but these methods are typically effective only in very particular circumstances, such as when the conductive elements have been completely dished or eroded.

Accordingly, improved detection systems allowing more precise characterization of erosion and dishing are desirable.

SUMMARY

The present invention includes a system for efficient and effective detection and characterization of dishing and/or erosion. An x-ray emission inducer is used to scan a target on a sample. The target can be scanned from different directions to allow characterization of the dishing and/or erosion and analysis of the metallization or thin film layer topology.

According to various embodiments, a system for characterizing dishing and/or erosion associated with a sample having a first surface and a second surface is provided. The system includes a memory and a processor. The processor is coupled with memory and is configured to identify a first measurement of induced x-ray emissions characteristic of a first material emitted upon scanning a first scan target from a first direction. The processor is further configured to identify a second measurement of induced x-ray emissions characteristic of the first material emitted upon scanning the first scan target from a second direction. The first and second measurements provide information for characterizing dishing and/or erosion associated with the sample.

According to other embodiments, an apparatus for characterizing dishing and/or erosion in a first scan target associated with a sample having a first surface and a second surface is provided. The apparatus includes an x-ray emission inducer configured to scan a first scan target at an acute incident angle. The x-ray emission inducer causes the first scan target to emit x-rays from the first surface. The apparatus also includes an x-ray emission detection system configured to obtain a measurement of the x-rays emitted from the first surface of the sample. The x-ray measurement is compared to a control measurement to provide information for characterizing dishing and/or erosion in the first scan target.

According to still other embodiments, a method for characterizing dishing and/or erosion in a sample is provided. The method includes identifying a first measurement of induced x-ray emissions characteristic of a first material at a first scan target resulting from a first scan from a first direction, identifying a second measurement of induced x-ray emissions characteristic of the first material at the first scan target resulting from a second scan from a second direction, and providing the first and second measurements to allow characterization of dishing and/or erosion associated with the first scan target in the sample.

These and other features and advantages of the present invention will be presented in more detail in the following specification of the invention and the accompanying figures which illustrate by way of example various principles of the invention.

BRIEF DESCRIPTION OF THE DRAWINGS

The invention may best be understood by reference to the following description taken in conjunction with the accompanying drawings. It should be noted that the drawings are illustrative of specific embodiments of the present invention.

DESCRIPTION OF SPECIFIC EMBODIMENTS

The techniques of the present invention allow nondestructive detection, isolation, and characterization of dishing and/or erosion in a test sample. In one embodiment, the test sample is a wafer comprising a plurality of integrated circuits. During the production of conventional integrated circuits, dishing and/or erosion of conductive elements may occur.

The present invention provides methods and apparatus for characterizing dishing and/or erosion. The techniques allow a determination of the significance of the defect. In one embodiment, an x-ray emission inducer such as an electron beam or an irradiation source is used to scan a test sample. The x-ray emission inducer can be configured to scan a target from a first direction. The scan can be conducted an acute incident angle as will be described further below. An x-ray detector is aligned near the x-ray emission inducer to detect x-rays emitted from the test sample. According to various embodiments, a conductive material exposed to a scan emits x-rays with emission energies corresponding to the conductive material. For example, copper bombarded by electrons emits x-rays characteristic of copper while tantalum bombarded by electrons emits x-rays characteristic of tantalum. The scanning of a dished or eroded conductive element would not emit as many characteristic x-rays as a piece of conductive material. An x-ray detector can measure the intensity of x-rays emitted at a scan target to determine characteristics of dishing and/or erosion at the scan target. Scanning from different directions allows determination of dishing and erosion characteristics including severity and depth at various locations.

With information about the characteristics of the defect, production process can be improved to reduce dishing and erosion and to increase yields.

Several embodiments of the present invention are described herein in the context of exemplary multilevel integrated circuit structures, including semiconductor structures and overlying metallization or other interconnects, using various levels of conductors that are separated from each other and the substrate by dielectric layers. However, structures formed using other methods of semiconductor fabrication also fall within the scope of the present invention. The techniques of the present invention apply to all surfaces with and without targets.

Figure 1:
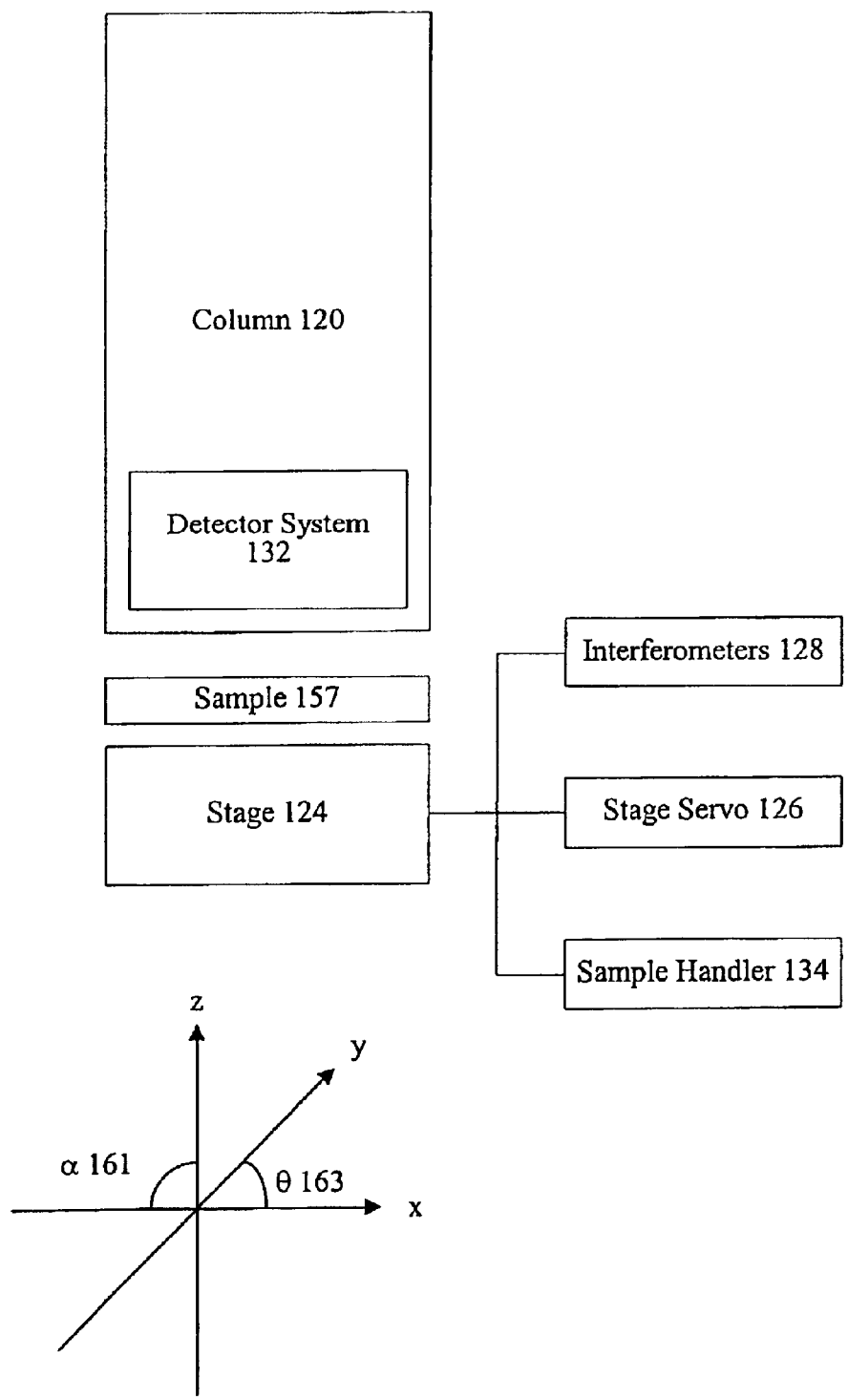
FIG. 1 is a diagrammatic representation of a system that can use the techniques of the present invention.

FIG. 1 is a diagrammatic representation of a system that can use the techniques of the present invention. The detail in FIG. 1 is provided for illustrative purposes. One skilled in the art would understand that variations to the system shown in FIG. 1 fall within the scope of the present invention. For example, FIG. 1 shows the operation of an x-ray emission inducer with a continuously moving stage. However, the test structures and many of the methods described herein are also useful in the context of other testing devices, including x-ray emission inducers operated in step and repeat mode. As an alternative to moving the stage with respect to the bean, the beam may be moved by deflecting the field of view with an electromagnetic lens. Alternatively, the beam column can be moved with respect to the stage.

Sample 157 can be secured automatically beneath an x-ray emission inducer 120. Any apparatus that is capable of causing a test sample to emit x-rays is referred to herein as an x-ray emission inducer. The x-ray emission inducer 120 can be a particle beam such as an electron beam or an irradiation source such as an x-ray emitter. The sample handler 134 can be configured to automatically orient the sample on stage 124. The stage 124 can be configured to have six degrees of freedom including movement and rotation along the x-axis, y-axis, and z-axis. In one embodiment, the stage 124 is aligned relative to the x-ray emission inducer 120 so that the x-directional motion of the stage corresponds to the axis determined by the size of a target. For example, the sample 157 can be aligned so that the x-directional movement of the stage corresponds to the length of a target as viewed from the top of the sample. Furthermore, sample can be tilted relative to the inducer 120 along the axis determined by the length of the target. Similarly, the sample 157 can also be aligned so that the x-directional movement of stage corresponds to the size of a target. The sample can be tilted relative to the electron beam along the axis determined by the size of the target.

In one example, the stage lies on the x-y plane and the stage is tilted by varying the angle $\alpha$ 161. It should be noted that tilting the sample relative to the inducer 120 can involve tilting the stage, moving the column, or deflecting the beam with a lens. It should also be noted that tilting the stage may involve varying the angle $\alpha$ 161 as well as rotating the stage along angle $\theta$ 163. Tilting the sample is one way of allowing scanning from different directions. Where the inducer 120 is an electron beam, the sample can be aligned so that electrons can impinge a scan target from a wide variety of different angles.

Arranging a scan target at a variety of different angles relative to the inducer 120 or the detector 132 allows a more thorough characterization of dishing and erosion. The yield of characteristic x-ray emissions, secondary electrons, and backscattered electrons all vary based upon the incident angle of the beam. By tilting a sample during the scan of a scan target and rotating the sample relative to the center of a target, a surface topography can be determined by measuring x-ray emissions at varies angles and various rotations. Secondary electrons and backscattered electrons can be measured as well.

Fine alignment of the sample can be achieved automatically or with the assistance of a system operator. The position and movement of stage 124 during the analysis of sample 157 can be controlled by stage servo 126 and interferometers 128.

While the stage 124 is moving in the x-direction, the inducer 120 can be repeatedly deflected back and forth in the y-direction. According to various embodiments, the inducer 120 is moving back and forth at approximately 100 kHz.

According to a preferred embodiment, an x-ray emission detector 132 is aligned alongside the x-ray emission inducer 120 at a 35 degree angle on the z-axis. As will be appreciated by one of skill in the art, a close arrangement of inducer 120 and detector 132 allows more accurate detection of x-ray emissions. The inducer 120 and detector 132 as well as other elements such as the stage can be controlled using a variety of processors, storage elements, and input and output devices.

Figure 2:
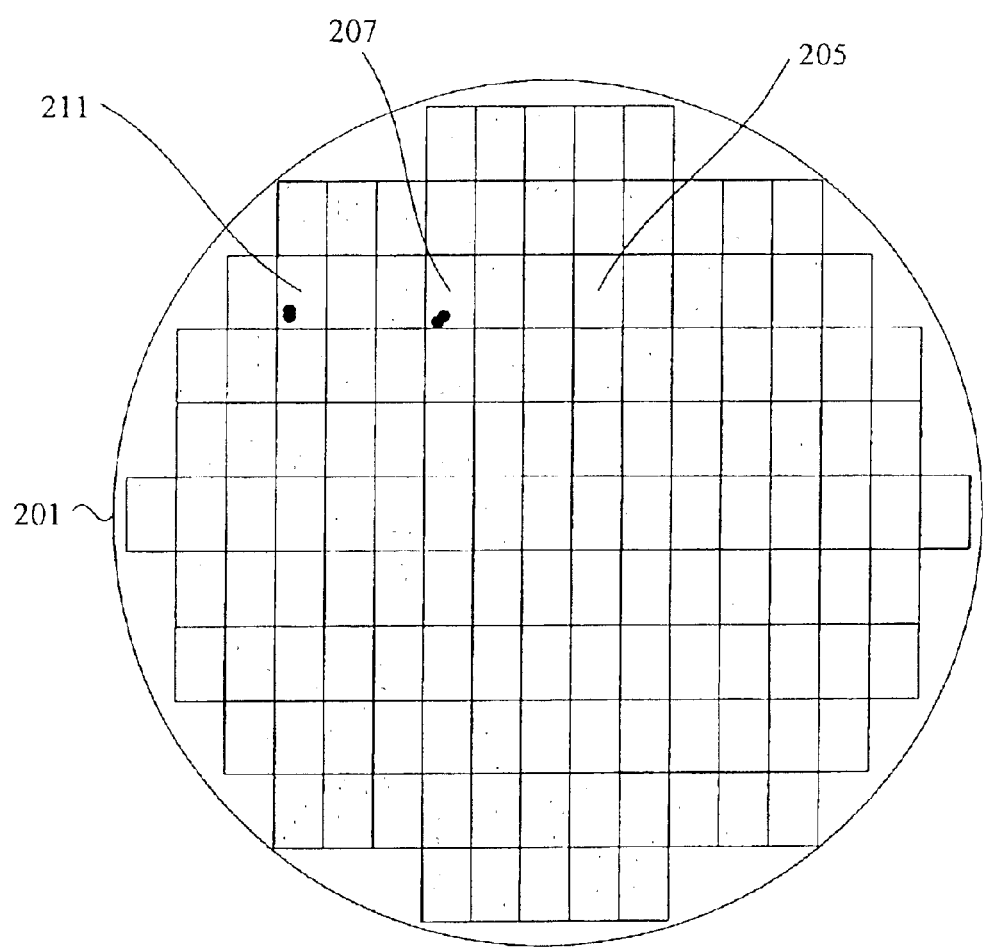
FIG. 2 is a diagrammatic representation of a wafer that may be the sample under test.

FIG. 2 is a diagrammatic representation of a wafer that may be a sample under test. A wafer 201 comprises a plurality of dies 205, 207, and 211. Die 205 contains no defects while dies 207 and 211 show erosion and/or dishing. According to various embodiments, the techniques of the present invention for erosion and dishing characterization are performed after each metallization or thin film layer is deposited onto a wafer. The side of the wafer where the metallization process is performed is herein referred as the first surface of the wafer. The wafer can be scanned to detect and characterize dishing and/or erosion after a thin film layer or metallization layer comprising a material such as copper is deposited onto the first surface of the wafer. The ability to detect erosion and dishing during the manufacturing process allows immediate modification of the manufacturing process. By contrast, conventional techniques often were unable to improve defective processes until after processing of the devices was completed.

The test methodologies of the present invention can be used as part of an advanced process control system, in which data from the testing process is provided to automated control systems for improving process yield. As an example, the techniques for dishing and erosion detection can provide data to automated control systems that dynamically improve the metallization processes.

Figure 3:
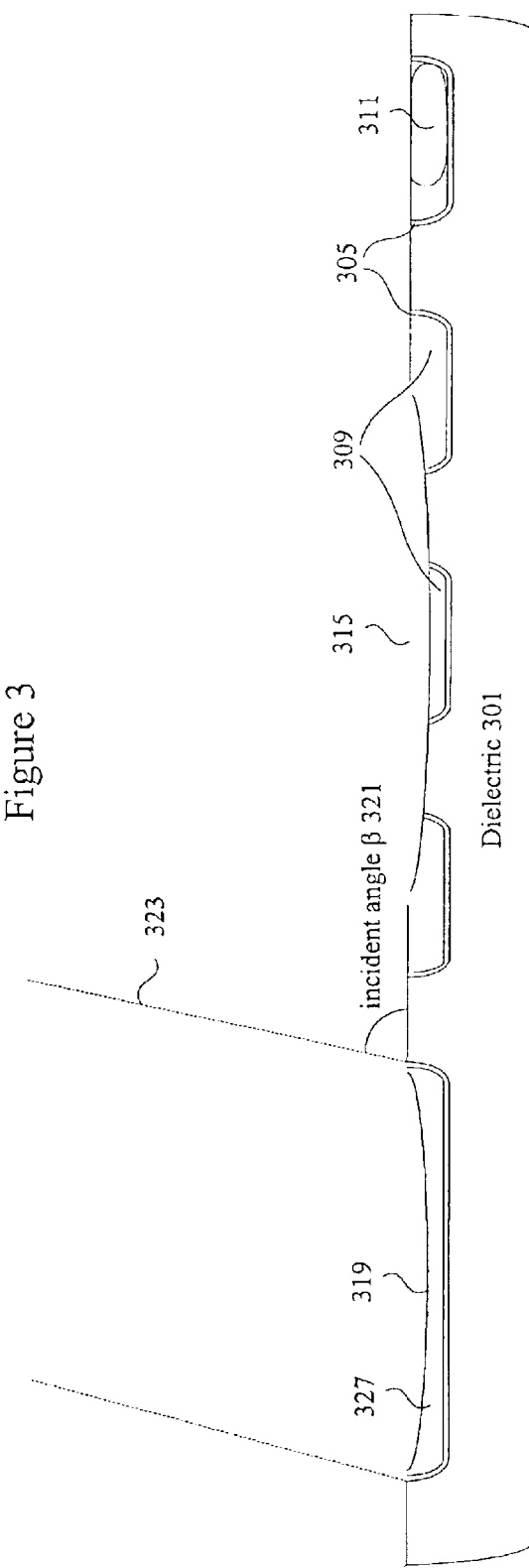
FIG. 3 is a diagrammatic representation showing a test sample.

FIG. 3 is a diagrammatic representation of a cross-section of a test sample. The metallization or thin film layer 309 is deposited on top of a barrier layer 305. According to various embodiments, the thin film layer 309 comprises a material such as copper (Cu) or aluminum (Al) and the barrier layer comprises a material such as tantalum (T) or tantalum nitride (TaN). Typically, the metallization or thin film layer 309 is much thicker than the barrier layer 305. A tantalum barrier layer 305 is typically used to prevent copper from thin film layer 309 from seeping into the dielectric 301. In one embodiment, the thin film layer is 1000 nm while the barrier layer is 15 nm. However, the techniques of the present invention can be used for detecting dishing 319 and erosion 315 associated with metallization layers 309 and barrier layers 305 of varying thickness.

According to one embodiment, target 327 shows characteristics of dishing 319. An electron beam 323 is used to scan target 327 and an incident angle β 321. According to various embodiments, incident angle β 321 is an acute angle measuring 60 degrees. Scanning the target 327 at an acute incident angle β 321 allows incident electrons to interact with conductive material to emit characteristic x-ray emissions. If the only conductive material remaining in a target is located along the edge of the target or alongside the dielectric 301, scanning from an acute incident angle would lead to fewer x-ray emissions than if more material remained in the center of the target.

Scanning the target 327 at different angles allows a characterization of the topology of the dishing 319 from different directions. The sample can also be rotated along the z-axis to allow scanning of the target 327 from various directions. In one example, the sample is rotated about the z-axis situated at the center of the target 327. According to another example, the sample is rotated about the z-axis determined by the center of the sample. The target 327 can be scanned at an acute incident angle β 321 by tilting the stage, moving the electron beam or varying an electromagnetic lens.

According to various embodiments, dishing and/or erosion is detected and characterized after a metallization layer 309 is deposited onto a barrier layer 305. The energy of the scan by an x-ray emission inducer such as an electron beam is varied based on the nominal thickness of the thin film layer. The electron beam energy is varied to generate the maximum x-ray emission intensity from the first surface of the sample. If the electron beam energy is insufficient, few electrons will penetrate the surface of the sample and interact with the conductive material, such as copper, to emit x-rays with energy levels characteristic of copper. As will be appreciated by one of skill in the art, electrons interacting with a conductive material such as copper emit K-line x-rays. Characteristic x-rays will be described further below.

If the electron beam energy is too high, many electrons will penetrate the conductive material completely and interact with an underlying barrier or dielectric material. X-rays may still be emitted due to interaction with a barrier or material such as tantalum, however the energy levels of the emitted x-rays will be characteristic of tantalum and not of copper.

Figure 4:
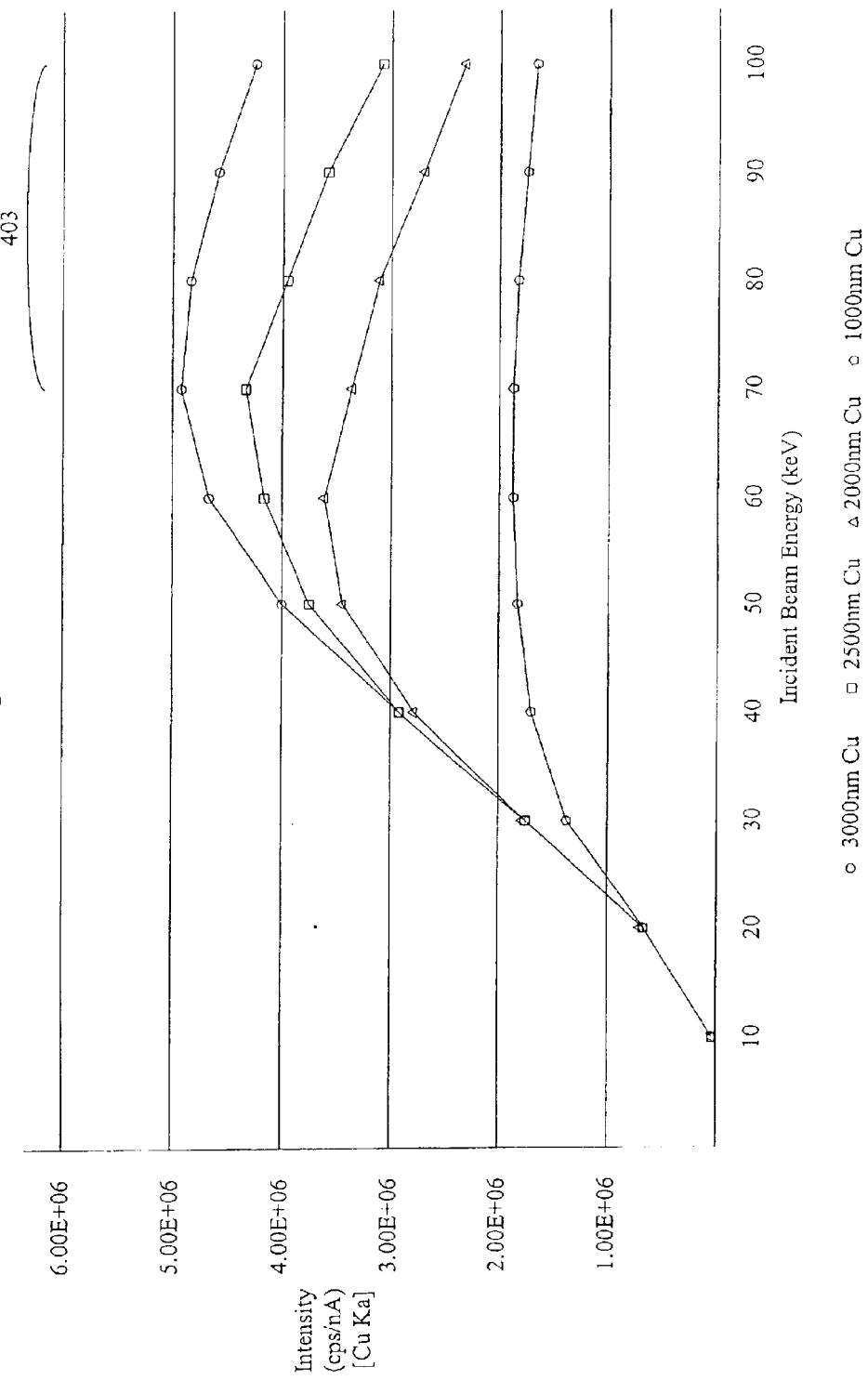
FIG. 4 is a graphical representation of incident beam energies and x-ray emission intensities.

Although the techniques of the present invention can be applied to characterizing dishing and/or erosion, they can also be applied to void characterization, as described in U.S. patent application Ser. No. 09/990,171 (Attorney Docket No. KLA1P041) by Mehran Nasser-Ghodsi and Anne Testoni, and titled Methods and Apparatus for Void Characterization FIG. 4 is a graphical representation showing preferred electron beam energies for copper layers of varying thickness. For 1000 nm copper, the x-ray emission intensity is 2.00e+06 cps/nA when the incident beam energy is approximately 40 keV For 2000 nm copper, the x-ray emission intensity is 3.50e+06 cps/nA when the incident beam energy is approximately 60 keV. It should be noted, that higher incident beam energies can be used for thicker copper layers. It should also be noted that higher beam energies eventually lead to a decrease in x-ray emission intensity as shown in portion 403.

As noted above, if the incident beam energy is too high, many electrons penetrate the metallization layer completely and interact with the underlying barrier or dielectric layers. Consequently, more x-ray emissions have energy levels corresponding to the underlying barrier materials. In one example, many electrons penetrate the copper layer and interact with the underlying tantalum barrier layer. The x-ray emission energies, consequently, correspond with x-ray emission energies characteristic of tantalum.

A similar effect would occur if there was dishing or erosion in the copper layer. If there was dishing or erosion, many electrons would penetrate through the copper layer entirely and interact with the underlying layers. More x-ray emissions characteristic of tantalum would be detected. This provides a convenient technique for confirming the existence of dishing and/or erosion. A scan target without dishing or erosion would produce many x-ray emissions characteristic of copper and fewer x-ray emissions characteristic of tantalum. However, a scan target with dishing and/or erosion would produce fewer x-ray emissions characteristic of copper and more x-ray emissions characteristic of tantalum, because the electrons would penetrate the copper layer entirely and interact with the underlying tantalum layer.

To detect x-ray emissions from different materials a single detector or a multiple detector can be used as the x-ray detection system. X-ray detection systems are described in more detail below. Detectors can also be arranged to measure secondary and backscatter electron emissions resulting from the scan of the scan target.

Another technique for detecting, characterizing, or confirming the existence of dishing and/or erosion is to measure the intensity of electrons that penetrate the test sample completely. Electrons penetrating the test sample completely can generate a current on an electrically isolated stage. Techniques for detecting and characterizing dishing and/or erosion by measuring generated current is described in U.S. patent application Ser. No. 09/990,170 (Attorney Docket No. KLA1P039) by Mehran Nasser-Ghodsi and Jeffrey Reichert, and titled Methods and Apparatus for Defect Localization.

Figure 5:
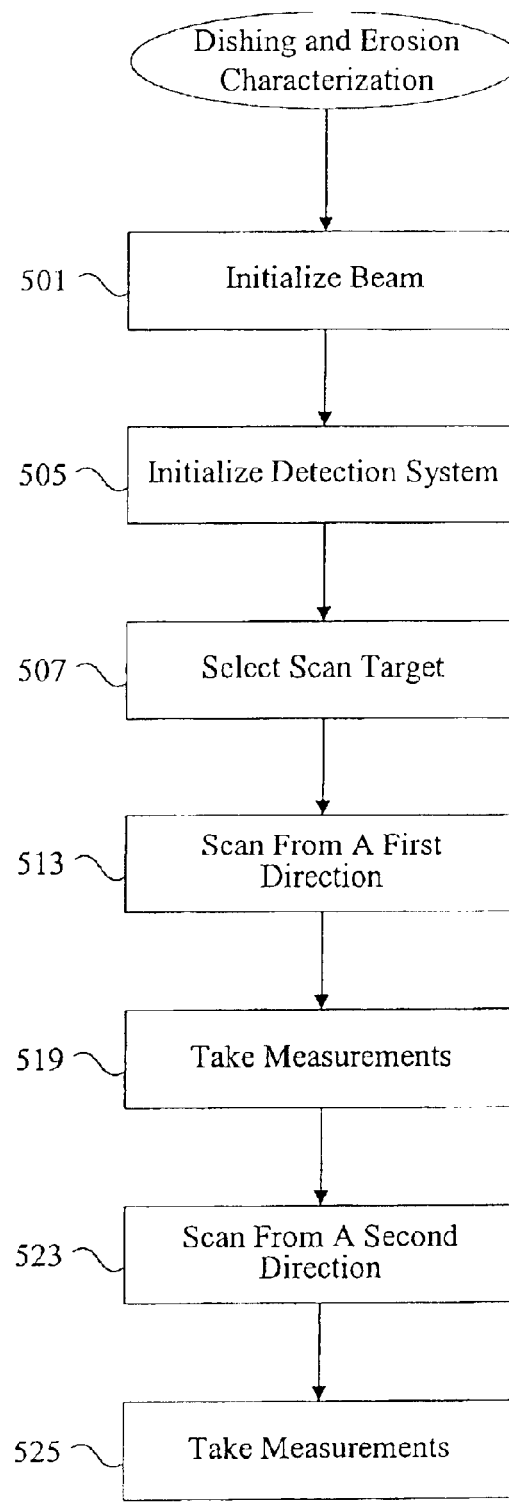
FIG. 5 is a process flow diagram showing the scanning of a sample.

FIG. 5 is a process flow diagram showing the detection and characterization of dishing and/or erosion according to specific embodiments. At 501, and x-ray emission inducer is initialized. Initializing the x-ray emission inducer may involve setting an electron beam energy based on the thickness of a thin film layer under test. The beam energy can be set as noted above with reference to FIG. 4.

The x-ray emission detectors can be initialized at 505. Initializing the detectors can include setting the detectors to measure characteristic x-ray emissions from particular materials such as copper or tantalum. As will be appreciated by one of skill in the art, the detectors can be spectrometers configured to detect K-line and L-line emissions. A standard sample can be scanned using the x-ray emission inducer as part of the initialization process at 505. In one embodiment, a layer of copper having a predetermined thickness is scanned so that characteristic x-ray emissions are measured by the detectors at 505. The standard measurement can be used to tune the x-ray detectors to set detector sensitivity. A variety of calibration and initialization techniques can be used. According to various embodiments, initialization of the inducer at 501 and the detectors at 505 is performed before each wafer is tested. According to other embodiments, initialization occurs again after a number of wafers are scanned. The detection system can be initialized to detect secondary and backscattered electrons as well.

At 507, the x-ray emission inducer is directed at the scan target. The scan target may be an area of interest as determined by the voltage contrast technique. The scan target may also be any area that may show dishing and/or erosion. The inducer can be directed at the scan target in a variety of different manners such as moving the stage or moving the inducer. At 513, a suspect target is scanned from a first direction by the the x-ray emission inducer. Centering the target may include orienting the long axis of the target with the x-axis of the stage. Centering the target may also include rotating or tilting the stage. According to one embodiment, the target is tilted so that the plane defined by the sample is perpendicular to the x-ray emission detectors and at a 35 degree angle with the x-ray emission inducer.

The target is scanned by an x-ray emission inducer, such as electron beam, and the x-ray emission intensity is measured at 519. According to various embodiments, the x-ray emission detector system is located alongside the x-ray emission inducer on the top side of the sample. In one embodiment, the target is then scanned from a second direction at 523. Measurements can be taken of x-ray emissions resulting from the scan from the second direction at 525. Scans from different directions allow analysis of the topology of the scan target.

In another embodiment, the x-ray emission counts are compared with a control measurement to characterize dishing or erosion in the target. If the x-ray emission intensity is 25% less than the control measurement, a dishing or erosion is determined to be present. In one example, if the x-ray emission intensity is 2.00E+06 cps/nA while the control measurement is 3.00E+06 cps/nA, dishing or erosion is determined to be present. The control measurement can be determined in a number of different ways. According to one embodiment, after the x-ray intensity is measured, the neighboring targets are scanned and the x-ray emission counts corresponding to the neighboring targets are determined. For example, after the first target is scanned and the x-ray emission counts determined, the neighboring +x, −x, +y, and −y targets are scanned and the corresponding x-ray emission counts measured. Subsequently, the neighboring +2x, −2x, +2y, −2y targets are scanned as well. As noted above, the x-ray emission counts corresponding to the neighboring targets can be used to determine a control measurement. Alternatively the control measurement may be a value stored in the database determined from another process or from scans of certain neighboring targets such as +x, +y, −x, −y, etc. In one embodiment, the x-ray emissions from a target and the x-ray emissions from adjacent targets can be compared graphically.

According to other embodiments, control measurements can be taken while the sample is being rotated. A scan can be focused on a particular target of interest. The sample can then be tilted to allow characterization of the topography of the metallization layer. Measurements of x-ray emissions can be taken while the sample is rotated. In another embodiment, the stage securing the sample remains stationary while an electron beam is configured to scan the target from a variety of different angles.

Scanning the target from different directions allows a more thorough characterization of dishing and/or erosion. Dishing or erosion of a metallization layer can often remove substantial amounts of conductive material. The remaining material may not emit sufficient x-rays to allow comparison and analysis of topological features.

Figure 6:
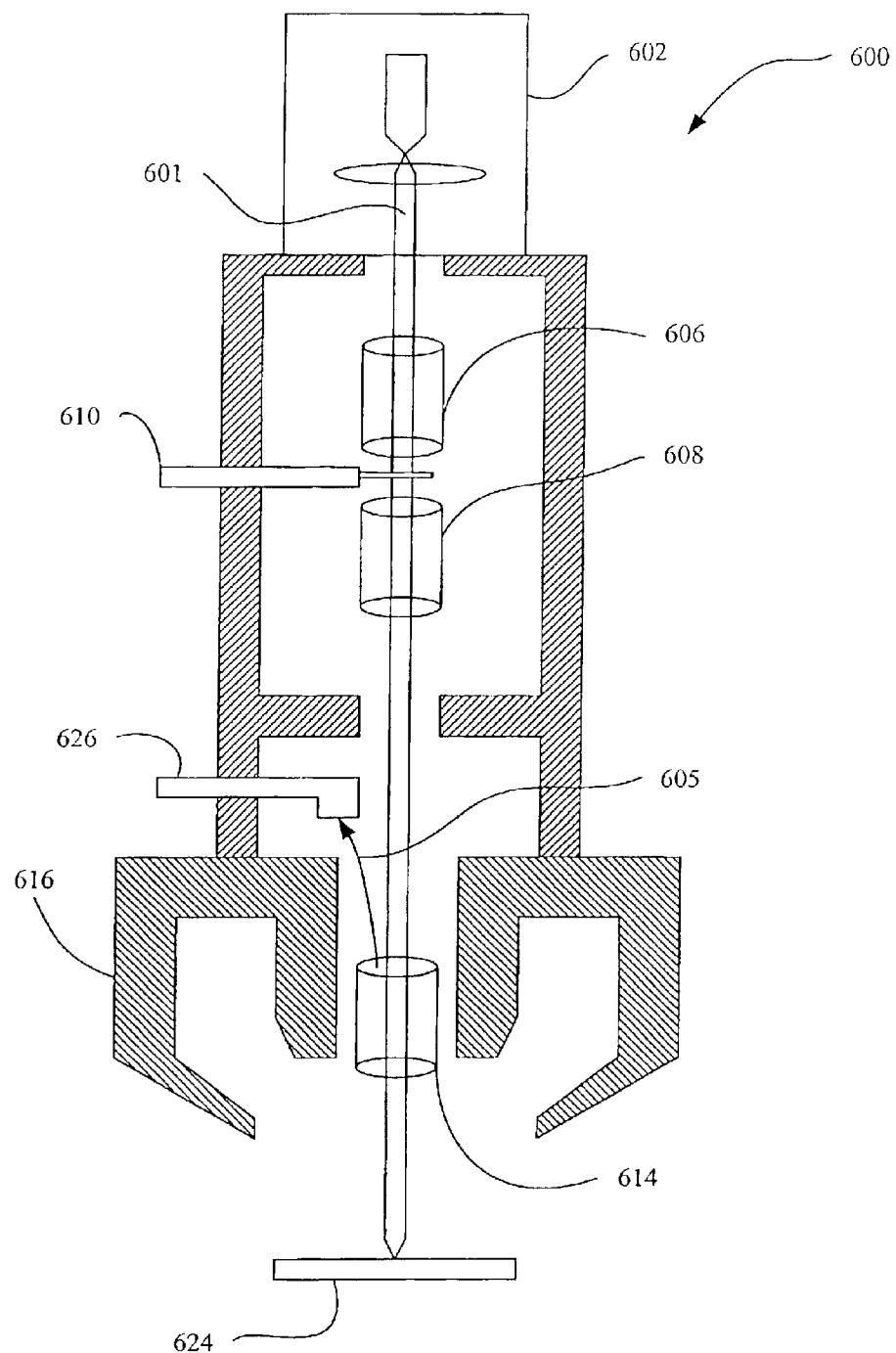
FIG. 6 is a diagrammatic representation of an electron beam that can be used to implement scanning of a sample.

An x-ray emission inducer may be anything that causes X-rays to emanate from the sample under test. In one embodiment, the x-ray emission inducer can be a scanning electron microscope (SEM). FIG. 6 is a diagrammatic representation of a scanning electron microscope (SEM) 600. As shown, the SEM system 600 includes an electron beam generator (602 through 616) that generates and directs an electron beam 601 substantially toward an area of interest on a specimen 624.

In one embodiment, the electron beam generator can include an electron source unit 602, an alignment octupole 606, an electrostatic predeflector 608, a variable aperture 610, a wien filter 614, and a magnetic objective lens 616. The source unit 602 may be implemented in any suitable form for generating and emitting electrons. For example, the source unit 602 may be in the form of a filament that is heated such that electrons within the filament are excited and emitted from the filament. The octupole 606 is configured to align the beam after a particular gun lens voltage is selected. In other words, the beam may have to be moved such that it is realigned with respect to the aperture 610.

The aperture 610 forms a hole through which the beam is directed. The lower quadrupole 608 may be included to compensate for mechanical alignment discrepancies. That is, the lower quadrupole 608 is used to adjust the alignment of the beam with respect to any misaligned through-holes of the SEM through which the beam must travel. The magnetic objective lens 616 provides a mechanism for accelerating the beam towards the sample.

Figure 7:
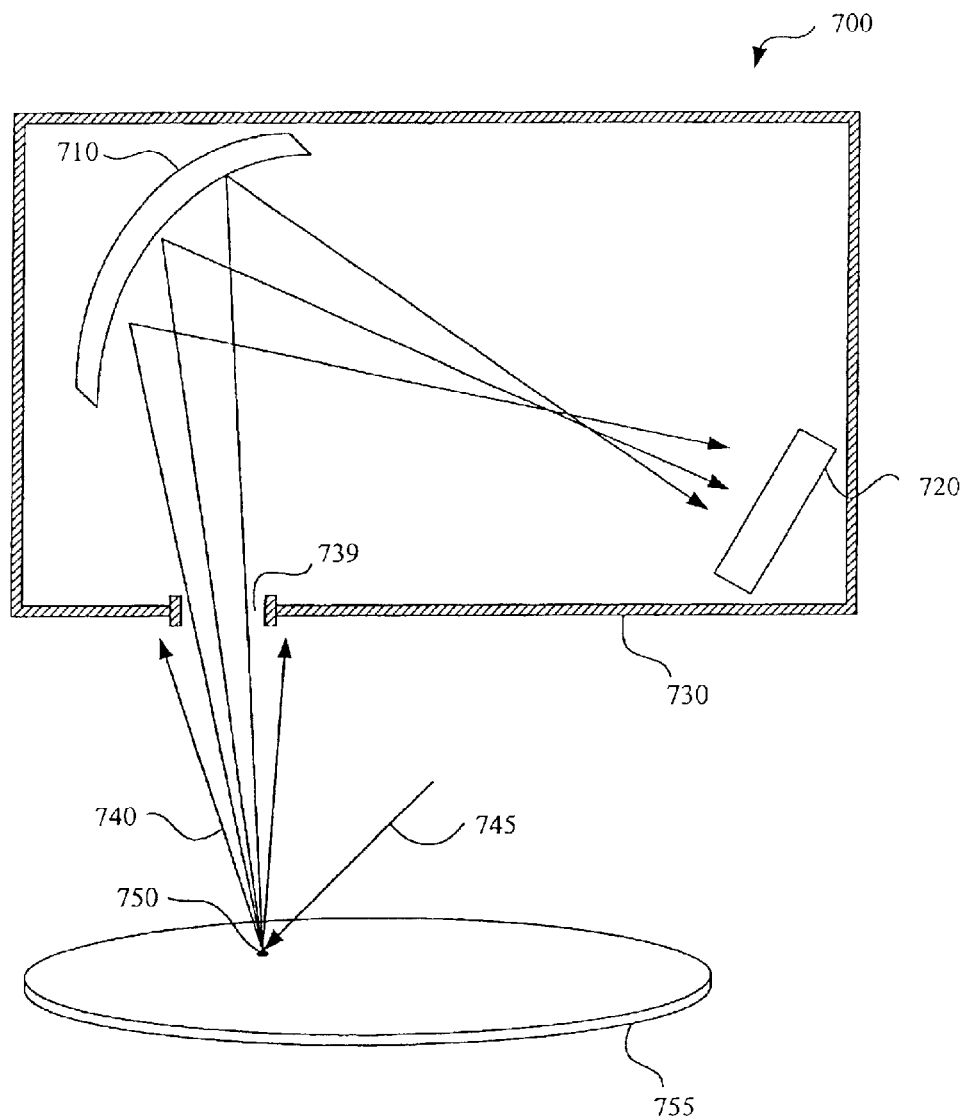
FIG. 7 is a diagrammatic representation of a detector that can be used to measure x-ray emissions.

Any suitable detector for measuring x-rays may be used to detect x-rays emitted from the sample. FIG. 7 is a cross-sectional representation of a wavelength dispersive system (WDS) x-ray detector in accordance with one embodiment of the present invention. Each x-ray detector 700 includes a housing 730 having an aperture 735. The housing and aperture are optional for practicing the techniques of the present invention. An electron beam 745 is directed to a focus point 750 on a thin film device 755 (i.e., a semiconductor wafer). The electron beam 745 causes photons 740 to emanate from the focus point 750. The aperture 735 permits a limited amount of photons 740 to enter each detector 700. Upon entering the detector 700, each photon travels along a path to a concave reflective surface 710. The reflective surface 710 directs a portion of photons to a sensor 720. The reflective surface 710 is designed and positioned so that only photons with a specific energy level are directed to the sensor 720. The reflective surface 710 may be positioned to direct only photons with an energy level characteristic of a certain material to facilitate a film characterization process. By detecting photons of only a specific energy level, detector 700 is capable of obtaining high signal to noise ratios. It should be noted that the reflective surface may be a Bragg reflector or a crystal capable of directing photons towards the sensor.

Figure 8:
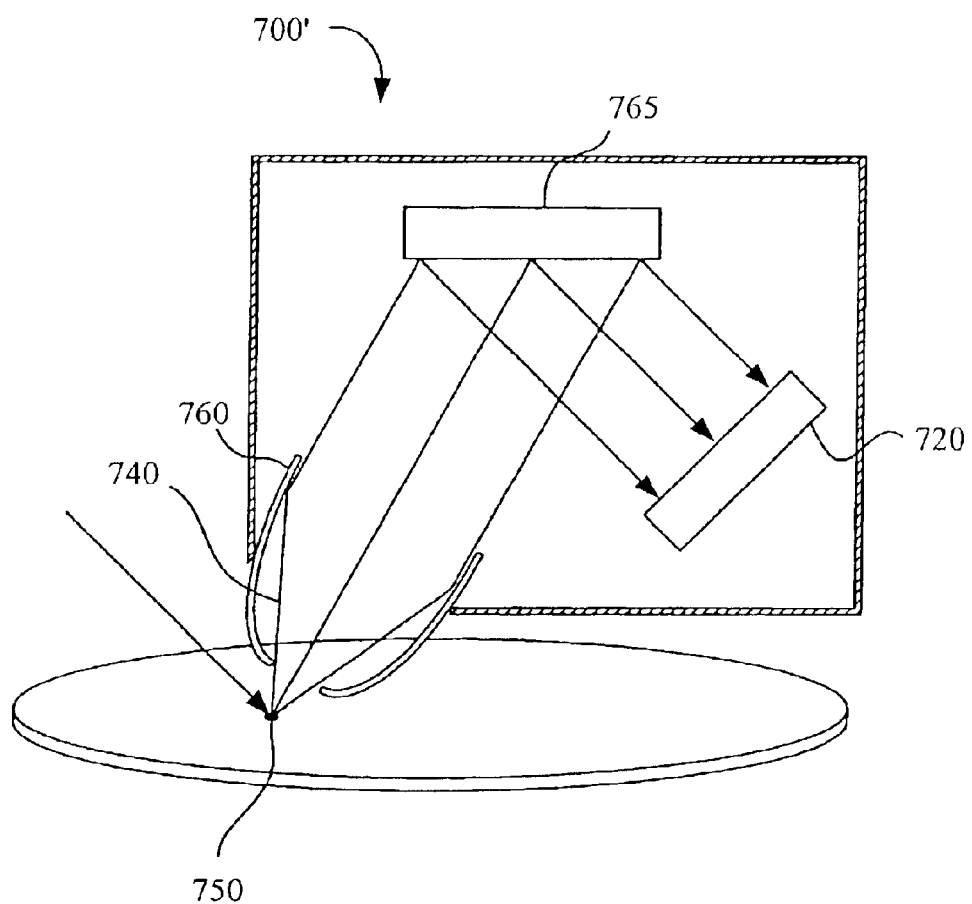
FIG. 8 is a cross-sectional view of a detector that can be used.

A cross-sectional view of an alternative embodiment of a WDS X-ray detector 700' is illustrated in FIG. 8. Detector 700' has a collimator 760 that captures the photons 740 emanating from the focus point 750, and then through its reflective surfaces causes the photons 740 to travel in substantially parallel paths. The collimator 760 is generally made from metal foil material. The photons then reflect off of a substantially flat reflective surface 765 such that the photons 740 continue in parallel paths towards the sensor 720. Similarly with detector 700, the reflective surface 765 in detector 700' may also be Bragg reflector or a crystal.

A common device which contains the general elements of the detector 700 and 700' is a Wavelength Dispersive System (WDS). By utilizing multiple WDS detectors, one or more photon peaks may be detected for each type of material that is expected to be present within the measured film stack of the specimen. That is, characteristic emission levels for one or more types of material in the film stack may be measured. One or more individual detectors may also be dedicated to detect the various characteristic emission levels for each type of material. For example, two WDS detectors may be dedicated for detecting two peaks associated with a copper material. As described earlier each material has emission levels characteristic of photons released due to an electron falling from each of the K, L, or M shells. By using multiple WDS detectors, the test system is able to obtain information for each of a multiple number of film layers.

Another type of detector, an Energy Dispersive System (EDS), collects photons in a wide spectrum of energies. EDS are capable of collecting a greater range of signals. As a result however, EDS detectors also collect photons having energies surrounding the characteristic photon energies. This causes EDS detectors to have lower signal to noise ratios.

The test system of the illustrated embodiment is capable of obtaining measurements having precision within 0.5% accuracy Thus, the test system allows for both accurate characterization and a high throughput rate.

Although the foregoing invention has been described in some detail for purposes of clarity of understanding, it will be apparent that certain changes and modifications may be practiced within the scope of the appended claims. The techniques of the present invention can be applied to dishing and/or erosion characterization, but can also be used for thin-film measurement as described in U.S. patent application Ser. No. 09/695,726 by Shing Lee, and titled Film Thickness Measurement Using E-Beam Induced X-Ray Microanalysis as of filing on Oct. 23, 2000, the entirety of which is incorporated herein by reference for all purposes.

It should be noted that there are many alternative ways of implementing the techniques of the present invention. For example, prior to performing comparisons between x-ray emission measurements and control measurements, an entire wafer may be scanned and the corresponding emission measurements stored. The comparisons can then be performed after the entire wafer is scanned and the control measurement can be determined using emission measurements from the entire wafer. Accordingly, the present embodiments are to be considered as illustrative and not restrictive, and the invention is not to be limited to the details given herein, but may be modified within the scope and equivalents of the appended claims.

What is claimed is:

1. A system for characterizing dishing and/or erosion associated with a sample, the sample having a first surface and a second surface, the system comprising:

memory;

a processor coupled with memory, the processor configured to identify a first measurement of induced x-ray emissions characteristic of a first material emitted upon scanning a first scan target at a first acute incident angle and identify a second measurement of induced x-ray emissions characteristic of the first material emitted upon scanning the first scan target at a second acute incident angle different from the first incident angle, wherein the first and second measurements provide information for characterizing dishing and/or erosion associated with the sample.

2. The system of claim 1, wherein the processor is further configured to identify a control measurement.

3. The system of claim 1, wherein the first material is copper.

4. The system of claim 1, wherein the sample is a wafer comprising a plurality of integrated circuits.

5. The system of claim 1, further comprising identifying a second measurement of x-ray emissions characteristic of a second material.

6. The system of claim 1, wherein the second material is a barrier material.

7. The system of claim 1, wherein the second material is Ta.

8. The system of claim 1, wherein the control measurement is obtained by scanning an adjacent scan target.

9. An apparatus for characterizing dishing and/or erosion in a first scan target associated with a sample, the sample having a first surface and a second surface, the apparatus comprising:

an x-ray emission inducer configured to scan a first scan target at a plurality of acute incident angles, the x-ray emission inducer causing the first scan target to emit x-rays from the first surface;

an x-ray emission detection system configured to obtain a measurement of the x-rays emitted from the first surface of the sample, wherein the x-ray measurement is compared to a control measurement to provide information for characterizing dishing and/or erosion in the first scan target.

10. The apparatus of claim 9, further comprising a stage configured to secure the sample, wherein the stage is configured to position the sample relative to the x-ray emission inducer.

11. The apparatus of claim 10, wherein positioning the sample comprises rotating the sample.

12. The apparatus of claim 10, wherein positioning the sample comprises tilting the sample along the axis formed by the sample and the x-ray emission inducer.

13. The apparatus of claim 10, wherein positioning the sample comprises tilting the sample along the axis formed by the sample and the x-ray emission inducer.

14. The apparatus of claim 13, wherein the sample is a wafer comprising a plurality of integrated circuits.

15. The apparatus of claim 14, wherein the x-ray emission detection system is configured to detect x-rays with a first emission energy corresponding to a first material.

16. The apparatus of claim 15, wherein the first material comprises Cu.

17. The apparatus of claim 16, wherein the x-ray emission detection system is further configured to detect x-rays with a second emission energy corresponding to a second material.

18. The apparatus of claim 17, wherein the second material comprises Ta.

19. The apparatus of claim 9, wherein the control measurement is obtained by scanning an adjacent scan target.

20. The apparatus of claim 19, wherein the control measurement is obtained by scanning a rotated scan target.

21. A method for characterizing dishing and/or erosion in a sample, the method comprising:

identifying a first measurement of induced x-ray emissions characteristic of a first material at a first scan target resulting from a first scan at a first acute incident angle;

identifying a second measurement of induced x-ray emissions characteristic of the first material at the first scan target resulting from a second scan at a second acute incident angle;

providing the first and second measurements to allow characterization of dishing and/or erosion associated with the first scan target in the sample.

22. The method of claim 21, further comprising identifying a control measurement.

23. The method of claim 21, wherein the first material has low resistivity.

24. The method of claim 21, wherein the first material is copper.

25. The method of claim 21, wherein the sample is a wafer comprising a plurality of integrated circuits.

26. The method of claim 21, further comprising identifying a second measurement of x-ray emissions characteristic of a second material.

27. The method of claim 21, wherein the second material is a barrier material.

28. The method of claim 21, wherein the second material is Ta.

29. The method of claim 21, wherein the control measurement is obtained by scanning an adjacent scan target.

* * * * *